(12) United States Patent
Pauly

(10) Patent No.: US 6,274,123 B1
(45) Date of Patent: Aug. 14, 2001

(54) USE OF AN EXTRACT OF THE GENUS ADANSONIA

(75) Inventor: Gilles Pauly, Nancy (FR)

(73) Assignee: Laboratories Serobiologiques, Pulnoy (FR)

(*) Notice: Subject to any disclaimer, the term of this patent is extended or adjusted under 35 U.S.C. 154(b) by 0 days.

(21) Appl. No.: 09/341,822

(22) PCT Filed: Jan. 16, 1998

(86) PCT No.: PCT/FR98/00084

§ 371 Date: Jul. 20, 1999

§ 102(e) Date: Jul. 20, 1999

(87) PCT Pub. No.: WO98/31336

PCT Pub. Date: Jul. 23, 1998

(30) Foreign Application Priority Data

Jan. 20, 1997 (FR) .................................... 97 00709

(51) Int. Cl.⁷ .............................. A61K 7/48; A61K 36/78; A61K 7/04; A61K 7/06
(52) U.S. Cl. .............................. 424/59; 424/61; 424/70.1; 424/70.9; 424/74; 424/725
(58) Field of Search .................................... 424/195.1, 59, 424/61, 70.1, 70.9, 74, 725

(56) References Cited

FOREIGN PATENT DOCUMENTS 0 781 545   7/1997 (EP) .

OTHER PUBLICATIONS

Computer Biosis Abstract 1977:239970 Woolfe et al. "J.Sci.Food Agric." (1977) 28, (6) PP. 519–529.*
Computer CABA Abstract 89:112395 Gaiwe Et Al "Intern. Jour. Crude Drug Research" (1989) vol. 27, No. (2) PP. 101–104, 1977.*

J. Woodruff, "Through The Natural Ingredients Maze", *Manufacturing Chemist*, vol. 65, No. 10, Oct., 1994, pp. 23–25.

J. Fabiyi et al., "Traditional Therapy of Dracunculiasis In the State of Bauchi–Nigeria", *Dakar Medical*, vol. 38, No. 2, 1993, pp. 193–195, AN 95278136.

A. Ramadan et al., "Anti–Inflammatory, Analgesic and Anti–pyretic Effects of the Fruit Pulp of Adansonia Digitata", *Fitoterapia*, vol. 65, No. 5, 1994, pp. 418–422, AN 94343891.

C.P. Locher et al., "Anti–Microbial Activity and Anti–Complement Activity of Extracts Obtained From Selected Hawaiian Medicinal Plants", *Journal of Ethnopharmacology*, vol. 49, No. 1, 1995, pp. 23–32, AN 9601644.

* cited by examiner

*Primary Examiner*—Herbert J. Lilling
(74) *Attorney, Agent, or Firm*—Young & Thompson

(57) ABSTRACT

A method and product effecting, in the skin, hair, eyelashes or nails of a human, an effect which can be emollient, softening, insulating, repair, hydration, soothing, emulsifying, nutrient, regenerative, anti-free radical, local anti-inflammatory, protective, photoprotective against UVB and UVA, anti-pollutant, anti-toxic, anti-sensitizing or inhibition of enzymes. There is applied to the skin, hair, nails or eyelashes of a human in need thereof, an effective amount of at least one material removed from the leaves of a plant of the genus Adansonia belonging to the family of Bombacaceaes by steeping in a liquid solvent and then removing the liquid to leave a dry material, the amount being effective to produce that effect. The plant is preferably *Adansonia digitata* or *baobab*.

6 Claims, No Drawings

USE OF AN EXTRACT OF THE GENUS ADANSONIA

FIELD OF THE INVENTION

The present invention relates to the field of cosmetology and dermatology, and has for its object the use for cosmetic, dermatologic or pharmaceutical applications, of a plant extract of the genus Adansonia, more particularly of the species *Adansonia digitata* (*baobab*), as well as a cosmetic and/or pharmaceutical product or composition for the skin and/or the hair, eyelashes or nails, comprising such an extract.

BACKGROUND OF THE INVENTION

*Baobab* (*Adansonia digitata*) is a deciduous tree, coming from the dry parts of central Africa and appears mostly in tropical countries, principally as a component of secondary forests.

The origin of plants of the genus Adansonia is probably located in Madagascar where several endemic species have been described and where *Adansonia digitata* also exists. Other species of the mentioned genus have been found in east Africa and in Australia.

The different constituent parts of baobab were and still are used and exploited in Africa, either from an economic standpoint (the bark for the production of fibers and paper, the wood has a rubber coagulant and the roots as a red coloring material), or as food (more particularly seeds and young leaves) or again as medicine (the bark has astringent diaphoretic and even febrifugic properties; the wood and the seeks have antidysenteric and anti-inflammatory properties; the leaves are used as an antiperspirant, against kidney and bladder troubles and as an anti-asthmatic and emollient).

It is known that the leaves contain particularly mucilages which swell in the presence of water.

*Baobab* leaves (D. YAZZIE et al., Journal of Food Composition and Analysis, 1994, 7; 3, 198–19313 R. GAIWE et al., International Journal of Crude Drug Research, 1989, 27, 2, 101–104) contain, in addition to mucilages, mineral salts, proteins, catechic tannins and vitamin compounds (riboflavin, thiamine, vitamin C, niacin); a flavonoid-type compound has also been discovered.

Analysis of the amino acid composition indicates that the proteins of the leaves of *baobab*, which represent about 10.6% of the dry weight of the leaves, contain interesting quantities of the following essential amino acids: lysine, arginine, threonine, tyrosine, phenylalanine, tryptophane, methionine and cysteine.

These leaves constitute quantitatively and qualitatively a good source of food proteins.

Moreover, *baobab* leaves contain high quantities of calcium (3.07 to 30 mg/g of dry leaves) and substantial quantities of iron, potassium, magnesium, manganese, molybdenum, phosphorus and zinc.

The dry extractable mucilage content of the leaves varies and is of the order of 9 to 12% relative to the dry leaves, the principal constituents of these mucilages having molecular weights higher than 100,000.

A high interaction between the proteins and the polysaccharides is supposed.

According to the literature (M. L. WOOLFE et al., J. Sci. Fd. Agric., 1977, 28, 519–529), the chemical composition of the mucilages of baobab leaves has been established as follows:

40.2 g galacturonic acid/100 g of mucilages
39.1 g glucuronic acid/100 g of mucilages
9.3 g of neutral sugars/100 g of mucilages.

These neutral sugars, which are rhamnose, galactose, glucose and arabinose, are present in a mole ratio of 0.6–1–0.44–0.15.

The above data indicate a very high portion of uronic acids and few neutral sugars: these mucilages do not have pectic compounds or pectic type units.

Moreover, these mucilages have interesting rheologic properties, their viscosity decreasing with an increase in the temperature of extraction.

SUMMARY OF THE INVENTION

However, the inventor of the present invention has determined, in an unexpected and surprising manner, that the extracts of plants of the Adansonia type, and more particularly extracts enriched in mucilages, have immediate properties more varied and quantitatively substantially greater than those of the polysaccharides already used in cosmetology or pharmacology, as well as long term effects and finally a very high tolerance.

OBJECTS OF THE INVENTION

Thus, the principal object of the present invention consists in the use or application of at least one extract of a plant of the genus Adansonia belonging to the family of Bombacaceaes for the preparation of a cosmetic and/or pharmaceutical product for topical use for the skin and/or the hair, eyelashes and nails.

DETAILED DESCRIPTION OF THE INVENTION

Preferably, the extract used is an extract of a plant belonging to the species selected from the group comprised by *Adansonia digitata, Adansonia fony, Adansonia gregorii, Adansonia madagascariensis, Adansonia grandidieri, Adansonia suarezensis* and *Adansonia za*.

According to a preferred embodiment of the invention, the mentioned extract is obtained from fresh or dried leaves (for example reduced to powder), preferably of *Adansonia digitata* or *baobab*, the extraction being carried out according to conventional extraction techniques, such as hot or cold extraction, with a solvent selected from the group consisting of water, aqueous solutions (neutral, acidified or alkaline), alcohols and mixtures of two or several of the mentioned solvents.

According to a first modification of embodiment of the invention, the extract used is a total extract of leaves, particularly of baobab, containing all the active ingredients contained in said leaf.

This total extract can be dried by techniques known to those skilled in the art such as lyophilization or atomization.

According to a second modified embodiment of the invention, it is possible to proceed with supplemental operations of purification (for example by precipitation in organic solvents) permitting to obtain on the one hand an extract consisting of one or more purified mucilages or an extract enriched in mucilages obtained from leaves, particularly of *baobab*, and/or, on the other hand, an extract consisting of a co-product of the extraction and/or purification of mucilages from leaves, particularly *baobab*, said co-product constituting a directly usable fraction rich in flavonoids, mineral salts, proteins, vitamins and/or other like compounds, such as particularly tannins.

It has also been discovered, in an unexpected and surprising manner, that when the process of extraction or purification comprises a step of treatment with a glycolytic enzyme of the β-glycosidase type, the mucilage or mucilages or extract rich in mucilage or mucilages that results has increased stability in solution.

By way of non-limiting example, there will hereafter be described different possible processes for obtaining an extract of *baobab*, particularly mucilages, which can be used within the scope of the present invention.

EXAMPLE 1
(production of type I extract)

2.2 Kg of leaves of *Adansonia digitata* are crushed in a bladed crusher and pass through a screen of 5 mm, 2.00 kg of leaf powder are thus obtained.

In a vat provided with an agitator, there is introduced 20.00 kg of distilled water and then the following operations are successively carried out:

raising the temperature to about 70° C., introducing with agitation the 2.00 kg of crushed and screened leaves, increasing the temperature to 90–95° C., extracting for one hour with agitation, cooling, centrifuging for 10 minutes at 5,000 g, recovering the supernatant (15.4 liters) which has a viscous appearance, a brown color and comprises 2.6% by weight of dry extract.

Purified mucilages can be obtained by using the following treatments of the above supernatant:

precipitating mucilages by addition of the supernatant with vigorous agitation, into 0.6 volume of absolute ethanol; formation of fibers which wind up about the agitator and hydroalcoholic supernatant brown in color, letting stand 2 hours in this medium, recovering the fibers, drying them on a filter cloth, washing the polysaccharide fibers in 1.6 liters of acetone (this treatment can be repeated), drying the fibers, spreading them out and drying them in open air then in an oven at 50° C., comminuting the dry mucilages in a bladed comminutor.

The weight of mucilage obtained is 168 grams, namely a yield of Y=8.4% by weight relative to the crushed leaves and a yield of about 7.6% by weight relative to the whole leaves (with stems).

EXAMPLE 2
(production of type 2 extract)

In a vat provided with an agitator, there is introduced 25.00 kg of distilled water and the following operations are successively carried out:

the temperature is raised to about 70° C., there are introduced with agitation 2.00 kg of crushed and screened leaves with vigorous agitation, the temperature is raised to 90–95° C., extraction with stirring is carried out for an hour, cooling, centrifuging for 10 minutes at 5,000 g, collecting the supernatant (16.9 liters) which has a viscous appearance, brown color and comprises 2.3% by weight of dry extract, holding the supernatant at 4° C. for hydrolysis.

A determination of the mucilage content of the solution can be carried out by precipitation of 200 ml of supernatant in a volume of ethanol, washing in acetone and drying the obtained precipitant. The concentration of mucilage in the extract thus determined is 9.15 g/l, namely a yield of mucilage Y=7.7% by weight relative to the powder of crushed leaves.

Purification of the mucilage of the extract obtained above can be carried out by using the following steps:

placing the viscous extract in a reactor provided with a pH electrode, adjusting the pH of the solution to 5.0, increasing the temperature to 25° C., adding to the solution an enzyme of the glucanase type at a dosage level of 10% relative to the mucilage, determined by alcoholic precipitation, hydrolyzing for 5 hours at a temperature of 50–55° C. and a pH of about 5.0, inactivating the enzyme by heating for 20 minutes at 100° C., cooling to ambient temperature, centrifuging, collecting the supernatant (14.73 liters), precipitating the mucilage by addition of the supernatant with violent agitation into one volume of absolute ethanol, treating the precipitate according to Example 1.

The weight of mucilage recovered is 132.7 grams, namely a yield of Y=6.6% by weight relative to the initial crushed leaves.

EXAMPLE 3
(production of type 3 extract)

There is filtered 1.9 liter of hydroalcoholic supernatant obtained from the precipitation of mucilage in Example 2 (dry extract=1.1%) on a clarifying filter 0.5 µm.

The theoretical yield in raw material (taking account of the dry extract and of the total volume of hydroalcoholic supernatant) is 7.76%/powder of leaves.

The following supplemental treatments are then applied to the filtered supernatant:

evaporation of the alcohol of the extract with a rotating evaporator (temperature of 40° C.), obtaining 0.91 liter of aqueous phase with a dry extract of 2.2%, if desired, addition of 40 g of dehydration adjuvant, atomization or lyophilization, obtention of 39.9 g of atomisate, namely an atomization output of 66.5%.

Testing for the presence of flavonoid compounds in the above product according to a known process (H. WAGNER et al., Plant Drug Analysis, p. 172, Springer Verlag 1984), carried out by use of the following migration solvents: ethyl acetate/formic acid/glacial acetic acid/water (100/11/11/27).

The detection of flavonoids is carried out with diphenyl-boric-acid-2-amino-ethyl ester of 1% in methanol/PEG 4000 of 5% in absolute ethanol.

Reading is carried out with a UV lamp, 365 nm.

It displays in the co-product a compound of orange color after vaporization of the reagent and observation at 365 nm whose Rf (0.39) is near that of rutine (0.40).

There are also observed 4 pockets of orange, blue and yellow color whose Rf are comprised between 0.095 and 0.18.

The present invention also has for its object cosmetic and/or pharmaceutical products or compositions for the skin and/or the hair, eyelashes and nails, characterized in that it comprises between 0.01% and 50.00% by weight of a plant extract of the genus Adansonia, particularly *baobab*.

Preferably, these products consist of a treatment compound comprising between 0.01% and 20.00% by weight of extract, particularly extract of leaves of *baobab*.

In these compositions or products for care of the skin, hair, eyelashes and nails, the mucilages, proteins and mineral salts extracted from plants of the genus Adansonia, and particularly *baobab*, have been preferably used as active emollients, softeners, insulators, repairers, hydrators, soothers, elastifiers, nutrients and regenerators of barrier properties.

The flavonoid co-products can be used in skin and hair care products as active vitamin P factors, anti-free radicals, and local anti-inflammatories, soothing agents, protectors, photoprotectors against UVB and UVA, anti-pollutants, anti-toxics, anti-sensitive skin and inhibitors of enzymes such as: elastase, hyaluronidase, histidine decarboxylase, phosphodiesterase of AMPC, lipo-oxygenase, tyrosinase or the like.

These complete active extracts of a plant of the Adansonia type (particularly *baobab*), in which the active purified transformed fractions such as mucilages, proteins, flavonoids, calcic mineral compounds or the like, can be present in the form of anhydrides, in the form of aqueous solutions or hydroglycolides, or again in time-released galenic form or with different actions (liposomes, nanosphere, microspheres, microcapsules or the like).

The extracts according to the invention are adapted to be incorporated in the most diverse cosmetic and/or pharmaceutical forms, such as particularly lotions, gels, hydrogels, oil/water emulsions, water/oil emulsions, micro-emulsions, skin care products, capillary care products or the like.

To demonstrate the beneficial effects of the extracts of leaves of Adansonia according to the invention, and more particularly those of the co-product of purification of the mucilages not only as to cosmetics but also as to biologics, the inventor has carried out various "in tubo" and "in vitro" tests of such a leaf extract (hereinafter called 114-I) obtained by means of the process described in the above Example 3.

The objects sought, the operative modes used and the results obtained within the scope of these tests are set forth briefly in what follows.

I) Anti-Free Radical Tests "in tubo"

The anti-free radical capacities are evaluated by a battery of tests covering not only the initial radical forms but also the reactive forms of oxygen ($HO^\circ$ and $O_2^{\bar{\circ}}$) induced in vivo.

Anti-DPPH Test:

DPPH (diphenylpicryl-hydrazyl) is a stable-free radical and colored violet, which is transformed to its leucoderivative by substances which capture and neutralize free radicals (=so-called "scavenger" effect).

In this test, the optical density is measured at 513 nm. Results (average of 2 tests):

| Doses in % (w/v) | Amount of Leucoderivative Formed (in %/Sample) |
|---|---|
| Sample | 0 |
| 114-1 at 0.003% | 28 C150 = 0.0124% (w/v) |
| 114-1 at 0.03% | 91 |
| 114-1 at 0.3% | 100 |

Anti-$HO^\circ$ Test with Salicylic Acid:

$HO^\circ$ (formed by $H_2O_2$ in the presence of $Fe^{++}$ and EDTA) is shown by salicylic acid.

Salicylic acid is hydroxylated by $HO^\circ$ into a pink compound and the quantity of hydroxylated salicylic acid corresponds to the optical density at 490 nm.

Results (average of 2 tests):

| Doses in % (w/v) | Amount of Hydroxylation with EDTA |
|---|---|
| Sample | 100 |
| 114-1 at 0.03% | 92 C150 = 0.24% (w/v) |
| 114-1 at 0.3% | 38 |

Anti-$HO^\circ$ Test with Desoxyribose $HO^\circ$ (formed by $H_2O_2$ in the presence of $Fe^{++}$ and EDTA) is disclosed by desoxyribose (this so-called Fenton reaction is also carried out without EDTA to measure the capacity to complex iron).

Desoxyribose is oxidized by $HO^\circ$ into andehydic derivatives measured with thiobarbituric acid, thiobarbituric acid forming by condensation with the aldehydes a roseate compound (optical density measured at 532 nm)

Results (average of 2 tests):

| Doses in % (w/v) | Aldehyde formed with EDTA | Aldehyde formed without EDTA |
|---|---|---|
| Sample | 100 | 100 |
| 114-1 at 0.03% | 99 C150 = 0.33% (w/v) | 76 C150 = 0.16% (w/v) |
| 114-1 at 0.3% | 55 | 21 |

Anti-Superoxide anion Tests $O_2^{\bar{\circ}}$ $O_2^{\bar{\circ}}$ is produced by an enzyme induced during oxidative stress: xanthine oxidase, which catabolizes the puric bases (adenine, guanine) in uric acid and $O_2^{\bar{\circ}}$.

Then $O_2^{\bar{\circ}}$ disassociates spontaneously (or by SOD= superoxide dismutase) into $H_2O_2$ and $O_2$.

Results (average of 2 tests):

a) $O_2^{\bar{\circ}}$ displays luminescence with luminol

| Doses in % (w/v) | % Inhibition of Luminescence/Sample |
|---|---|
| Sample | 0 |
| 114-1 at 0.0003% | 10 C150 = 0.0011% (w/v) |
| 114-1 at 0.003% | 67 |
| 114-1 at 0.03% | 99 | b) $O_2^{-\circ}$ and $H_2O_2$ disclosed by luminol in the presence of microperoxidase

| Doses in % (w/v) | % Inhibition of Luminescence/Sample |
|---|---|
| Sample | 0 |
| 114-1 at 0.003% | 13 C150 = 0.0096% (w/v) |
| 114-1 at 0.03% | 62 | c) $O_2^{-\circ}$ and $H_2O_2$ disclosed by NBT (tetrazolium salt) (optical density measured at 540 nm)

| Doses in % (w/v) | % Inhibition of DO at 540 nm/Sample |
|---|---|
| Sample | 0 |
| 114-1 at 0.03% | 21 C150 = 0.1298% (w/v) |
| 114-1 at 0.3% | 67 |

II) Anti-UVA Cytoprotection of Human Fibroblasts, "in vitro" Survival

UVA penetrates the skin where it induces an oxidative stress characterized by lipoperoxidation of the cytoplasmic membranes.

The lipoperoxides break down into malonaldialdehyde which cross-links numerous biological molecules as proteins (inhibition of enzymes) and nucleic bases (mutagenesis).

To carry out the tests, the fibroblasts are seeded into a culture medium comprises fetal veal serum and the product 114-1 (in the medium defined with 2% serum) is added 72 hours after seeding.

After an incubation of 48 hours at 37° C. and $CO_2$=5%, the culture medium is replaced by a saline solution and the fibroblasts are irradiated with a dose of UVA (15 J/cm$^2$; tubes of the MAZDA FLUOR TFWN40 type).

At the end of irradiation, the quantity of MDA (malonaldialdehyde) is added to the supernatant saline solution and the quantity of proteins is measured in the fibroblasts.

The MDA is measured by the reaction with thiobarbituric acid and the proteins according to the so-called Bradford method.

Results (in % relative to the sample, the average of 2 tests, each in triplicate):

| Doses in % (w/v) | MDA | Proteins |
|---|---|---|
| Non-irradiated sample | 0 | 100 |
| Irradiated sample (UVA) | 100 | 65 |
| Medium + 114-1 at 0.005% | 60 | 61 |
| Medium + 114-1 at 0.010% | 45 | 59 |

III) Anti-UVB Cytoprotection on Human Keratinocytes Surviving "in vitro"

UVB triggers an inflammation (erythema, edema) by activation of an enzyme, namely phospholipase A2 or PLA2, which loosens arachidonic acid of phospholipids from the plasmic membrane.

Arachidonic acid is the precursor of prostaglandines which are mediators of inflammation, the prostaglandines E2 (=PGE2) being formed by cyclooxygenase.

To carry out the tests, keratinocytes are seeded into a medium of fetal veal serum and the product 114-1 (diluted in saline solution) is added 72 hours after seeding.

Immediately, the keratinocytes are irradiated with a dose of UVB (30 mJ/cm$^2$—tubes of the DUKE FL40E type).

After an incubation of 1 day at 37° C., $CO_2$=5%, the quantities of PGE2 and LDH are measured in the supernatant medium.

The number of adherent keratinocytes is determined (after trypsination) by a particle counter.

The quantity of PGE2 is determined by an ELISA test and an LDH test (lactate-deshydrogenase) by an enzymatic reaction.

Results (in % relative to the sample, the average of 3 tests, each done in duplicate):

| doses in % (w/v) | Number of Keratinocytes | Quantity of LDH released | Quantity of PGE2 released* |
|---|---|---|---|
| Non-irradiated sample | 0.77 (million/well) | 0 | 0 |
| Irradiated sample, (UVB) | 0.32 | 100 | 100 |
| Medium + 114-1 at 0.005% | 0.38 | 64 | 82 |
| Medium + 114-1 at 0.010% | 0.68 | 15 | 21 |

*= in % relative to the irradiated sample (= 100%) and non-irradiated sample (= 0%).

*=in % relative to the irradiated sample (=100%) and non-irradiated sample (=0%).

From the above results, it will be seen that the extract of baobab leaves analyzed and tested (product 114-1) has significant capacities as to:

capturing and neutralizing free radicals and reactive forms of oxygen (HO$^\circ$ and $O_2^{-\circ}$), said product 114-1 acting at least in part by the capture of iron ("iron deprivation effect");

reducing the quantity of lipoperoxidation induced by the UVA on human fibroblasts;

reducing the quantity of PGE2 and the cellular damage induced by UVB on human keratinocytes.

As to cosmetics, the sensory analysis permits detecting a substantial restructuring, softening and satinizing effect.

By way of non-limiting examples of practical embodiments of the invention, there will be described hereafter different cosmetic products or preparations comprising an extract of plants of the genus and Adansonia, particularly *baobab*.

EXAMPLE 1

A cosmetic product in the form of a hydro-protective gel for the face according to the invention could for example have a weight composition, constituted by fractions or phases A, B, C, D, E and F as follows, as indicated hereafter.

| Fraction A: | |
|---|---|
| Distilled water | 49.950% |
| Elestab 50 J | 0.500% |
| Carrageenan | 0.100% |
| Fraction B: | |
| Carbomer | 0.300% |
| Distilled water | 31.955% |

-continued

| Fraction C: | |
|---|---|
| Propylene glycol | 2.000% |
| Dimethicone copolyol | 3.000% |
| Fraction D: | |
| Triethanolamine, 20% in aqueous solution | 2.145% |
| Fraction E: | |
| Kathon CG (Rohm and Haas) | 0.050% |
| Fraction F: | |
| Total dehydrated aqueous extract of leaves of Adansonia digitata (type 1 extract) | 0.500% |
| Distilled water | 9.500% |

The process of preparation and production of the mentioned gel consists essentially in preparing separately the fractions A and B at 75° C. with turbine agitation, then cooling them to ambient temperature, preparing fraction F by dispersion of the dehydrated extract in 20 times its weight of water, adding to the fraction A successively the fractions B, C, D, E and F at ambient temperature and with turbine agitation and finally carrying out planetary agitation to homogenize.

EXAMPLE 2

A cosmetic product in the form of a hydrating cream for sensitive skins, which will be non-polluting, according to the invention could, for example, have a weight composition, constituted by fractions or phases A, B and C as follows, as indicated hereafter.

| Fraction A: | |
|---|---|
| Tegin | 10.00% |
| Novata AB | 1.00% |
| Miglyol 812 | 8.00% |
| Cetiol | 5.00% |
| Eutanol G | 2.00% |
| Fraction B: | |
| Elestab 4112 | 0.35% |
| Distilled water | 60.65% |
| Glycerine | 3.00% |
| Fraction C: | |
| Dehydrated mucilaginous extract of Adansonia digitata (type 1 extract) | 1.00% |
| Distilled water | 9.00% |

The process of preparation and production of the mentioned cream consists essentially in preparing separately the fractions A and B at 75° C., preparing the fraction C by dispersion with turbine agitation, pouring fraction A at 75° C. into fraction B at 75° C. with turbine agitation, cooling the obtained mixture, with planetary agitation, to 50° C., and introducing fraction C.

EXAMPLE 3

A cosmetic product in the form of anti-wrinkle cream, anti-free radical cream, protective of collagen elastin and fundamental substance, anti-skin aging and that improves micro-circulation, according to the invention, could for example have a weight composition, constituted from fractions or phases A, B and C as follows, as indicated hereafter.

| Fraction A: | |
|---|---|
| Cutina CBS | 12.00% |
| Cutina E24 | 2.00% |
| Eumulgin B2 | 1.00% |
| Eutanol G | 3.00% |
| Cetiol SB45 | 3.00% |
| Cetiol SN | 4.00% |
| Fraction B: | |
| Glycerine | 5.00% |
| Distilled water | 47.50% |
| Elestab 388 | 2.50% |
| Vegeseryl HGP | 10.00% |
| Fraction C: | |
| Dehydrated flavonoidal extract of Adansonia digitata (type 3 extract) | 2.00% |
| Distilled water | 8.00 |

The process of preparation and production of the mentioned cream consists essentially in preparing separately the fractions A and B at 75° C., preparing fraction C by dispersion of the dry extract in four times its weight of water, pouring fraction A into fraction B with turbine agitation, cooling the mixture obtained, adding the fraction C at 50° C. and finally carrying out a single planetary agitation to ambient temperature.

EXAMPLE 4

A cosmetic product in the form of a capillary lotion to be vaporized and that is photoprotective, according to the invention could for example have a weight composition as indicated hereafter.

| | |
|---|---|
| Ethanol | 53.80% |
| Triethanolarnine | 0.10% |
| Gantrez ES425 | 3.60% |
| Glycerine | 1.00% |
| Flavonoid extract of leaves of Adansonia digitata (type 3 extract) | 1.00% |
| Panthenol | 0.50 |
| Propane/Butane | 40.00% |

The process of preparation and production of the mentioned capillary lotion consists essentially in mixing together the mentioned constituents, filtering the mixture obtained and packaging it with a propellant.

EXAMPLE 5

A cosmetic product in the form of soothing, repairing, hydrating, anti-edema, healing and radioprotective milk according to the invention could for example have a weight composition, constituted from fractions or phases A, B, C and D as follows, as indicated hereafter.

| Fraction A: | |
|---|---|
| Miglyol 812 | 8.00% |
| Jojobah Oil | 2.00% |

-continued

| | |
|---|---|
| Acetulan | 3.00% |
| Sphingoceryl VEG | 1.50% |
| Paraffin Oil | 5.00% |
| Brij 76 | 4.00% |
| Fraction B: | |
| Carbomer | 0.50% |
| Elestab 4112 | 0.40% |
| Sorbitol | 2.00% |
| Uvinul MS40 | 0.05% |
| Glucam E20 | 3.00% |
| Distilled water | 58.05% |
| Fraction C: | |
| Triethanolamine in 20% aqueous solution | 2.50% |
| Fraction D: | |
| Completely Dehydrated extract of leaves of Adansonia digitata (extract type 1 + extract type 3) | 5.00% |
| Distilled water | 5.00% |

The process of preparation and production of the mentioned after-sun milk consists essentially in preparing separately the fractions A and B at 75° C., pouring fraction A into fraction B with turbine agitation, adding fraction C, cooling, adding fraction D previously homogenized at 50° C. and cooling the obtained mixture with planetary agitation.

Of course, the invention is not limited to the described embodiment. Modifications remain possible, particularly as to the constitution of the various elements or by substitution of technical equivalents, without thereby departing from the scope of protection of the invention.

What is claimed is:

1. A cosmetic product for at least one of the skin, hair, eyelashes and nails of a human, comprising a composition containing between 0.50% and 20.00% by dry weight of a material removed from the leaves of a plant of the genus Adansonia belonging to the family of Bombacaceaes by steeping in a liquid solvent selected from the group consisting of the aqueous solution alcohols and mixtures thereof and then removing the liquid from the liquid extract to leave a dry said material, in admixture with a cosmetologically and dermatologically acceptable excipient.

2. A cosmetic product as claimed in claim 1, wherein said plant belongs to a species selected from the group consisting of *Adansonia digitata, Adansonia fony, Adansonia gregorri, Adansonia madagascariensis, Adansonia grandidieri, Adansonia suarezensis* and *Adansonia za*.

3. A cosmetic product as claimed in claim 1, wherein said plant is *Adansonia digitata* or *baobab*.

4. A method of effecting, in at least one of the skin, hair, eyelashes and nails of a human, an effect consisting of at least one of emollient, softening, insulating, repair, hydration, soothing, emulsifying, nutrient, regenerative, anti-free radical, local anti-inflammatory, protective, photo-protective against UVB and UVA, anti-pollutant, anti-toxic, anti-sensitizing and inhibition of enzymes, comprising applying to at least one of the skin, hair, nails and eyelashes of a human in need of the same, an effective amount of the cosmetic product of claim 1 containing at least one material removed from the leaves of a plant of the genus Adansonia belonging to the family of Bombacaceaes by steeping in a liquid solvent and then removing the liquid to leave a dry said material, said amount being effective to produce said effect.

5. A method as claimed in claim 4, wherein said plant belongs to a species selected from the group consisting of *Adansonia digitata, Adansonia fony, Adansonia gregorri, Adansonia madagascariensis, Adansonia grandidieri, Adansonia suarezensis* and *Adansonia za*.

6. A method as claimed in claim 5, wherein said plant is *Adansonia digitata* or *baobab*.

* * * * *